United States Patent [19]
Klar et al.

[11] 3,949,735
[45] Apr. 13, 1976

[54] METHOD AND APPARATUS FOR AN IPSILATERAL REFLEX TEST

[75] Inventors: Irwin Klar, New City, N.Y.; Arthur W. Rochussen, Nashua, N.H.

[73] Assignee: American Electromedics Corporation, Dobbs Ferry, N.Y.

[22] Filed: Aug. 20, 1974

[21] Appl. No.: 498,992

[52] U.S. Cl. .................. 128/2 Z; 73/553; 128/2 N; 179/1 N
[51] Int. Cl.² .......................................... A61B 5/12
[58] Field of Search .................. 128/2 Z, 2 N, 2 R; 179/1 N; 73/553

[56] References Cited
UNITED STATES PATENTS

| | | | |
|---|---|---|---|
| 2,415,310 | 2/1947 | Summerville et al. | 128/2 Z |
| 3,294,193 | 12/1966 | Zwislocki | 179/1 N X |
| 3,295,513 | 1/1967 | Dippolito | 128/2 Z |
| 3,395,697 | 8/1968 | Mendelson | 128/2 Z |
| 3,757,769 | 9/1973 | Arguimbau et al. | 128/2 Z |

*Primary Examiner*—Kyle L. Howell
*Attorney, Agent, or Firm*—Holland, Armstrong, Wilkie & Previto

[57] ABSTRACT

There is a well known clinical test of acoustic reflex in the human ear based upon a contraction of the stapedial muscle of the ear. The normal test method and equipment requires the use of test apparatus on both of the patient's ears. This test is replaced in the new method by a test method using a single probe which is applied to only one ear. The new acoustic reflex testing method subjects one ear to a probe tone and to a resulting relative compliance measurement. A stimulus tone is applied to the same ear to cause a contraction of the stapedial muscle which is indicated by a sharp change in the measure compliance at some stimulus tone level. In the new method of this invention, use is made of an observed delay between application of the stimulus and the contraction of the stapedial muscle. A switching system is used to obtain a second relative compliance reading during the delay period and after the stimulus has been turned off. The two relative compliance measurements are compared during the delay period and a signal is generated as soon as they differ significantly as a result of the stapedial muscle contraction.

16 Claims, 3 Drawing Figures

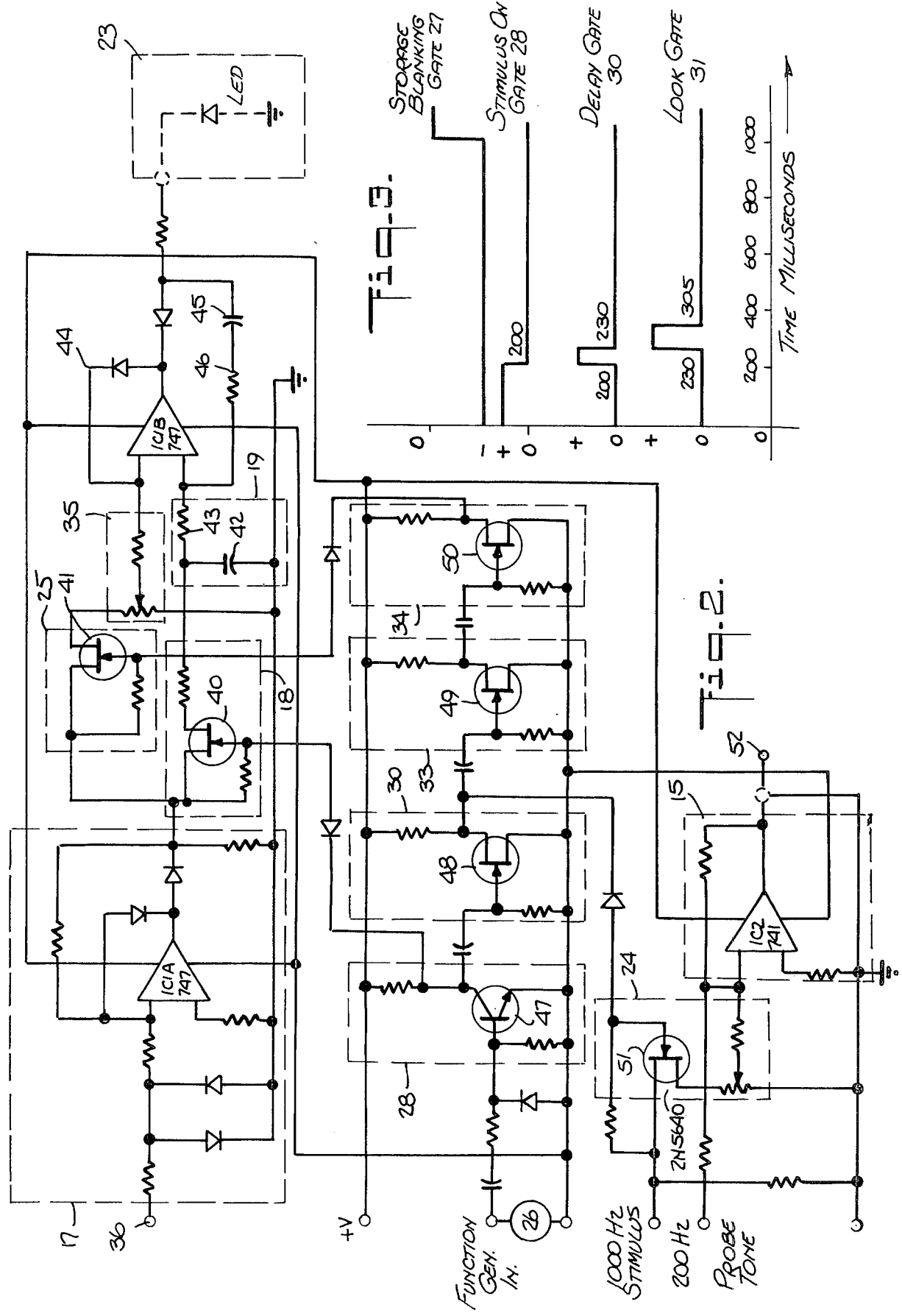

METHOD AND APPARATUS FOR AN IPSILATERAL REFLEX TEST

BACKGROUND OF THE INVENTION

The present invention relates to the clinical evaluation of hearing loss and more particularly to an improved acoustic reflex test which is one of a number of tests of the physical characteristics of the middle ear the results of which provide useful indications of the ear condition.

There are a number of clinical tests based upon the use of a probe or probes which are placed in the ears and where probe tones are used together with appropriate instrumentation to examine the functioning of the elements of the inner ear on a non-contact basis. One test which is being increasingly relied upon for determining certain essential characteristics of ears under test is known as an accoustic reflex test. This test is based upon the fact that the stapedial muscle contracts reflexively when it is subjected to a sufficiently loud stimulus tone. A measurement of the sound level at which this contraction occurs is used as a basis for important conclusions with regard to the ear under test. Known reflex testing uses apparatus requiring test devices on both of the patient's ears.

The improvements of the present method and related apparatus permit the test to be performed using a single probe in one ear only which results in increased test reliability with no reliance upon a bilateral ear response. Additionally, the use of a single probe in one ear provides for a simplified and more easily performed test with the preferred embodiments of the apparatus giving substantially automatic test results. This improved test may be designated as an ipsilateral reflex test. The ipsilateral reflex test method is preferably implemented utilizing time division multiplexing. Use is made of reflex latency which is the delay between the presentation of a stimulus tone to the ear and the subsequent reaction of the stapedious muscle. This inherent delay allows the stimulus tone to be presented and the effect of the muscle reaction to be determined subsequent to the turn-off of the stimulus. In this way, interaction between the stimulus signal and the measuring probe tone signal is eliminated by timing the opening of a gate to the reflex detector so that it occurs after the stimulus tone has been presented and the transients produced by it in the electrical circuit have subsided.

Accordingly, an object of the present invention is to provide an improved method and means for acoustic reflex testing.

Another object of the invention is to provide an improved method and means for acoustic reflex testing using a single probe applied to one ear.

Another object of the invention is to provide an improved acoustic reflex test utilizing the inherent delay observed in the response of the stapedious muscle to a stimulating signal.

Other and further objects of the invention will be obvious upon an understanding of the illustrative embodiment about to be described or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawing, forming a part of the specification, wherein:

FIG. 2 is a schematic diagram illustrating a preferred embodiment of the reflex test apparatus circuitry and FIG. 3 is a chart showing the gate timing relations.

DESCRIPTION OF THE PREFERRED EMBODIMEMT

Figure 1:
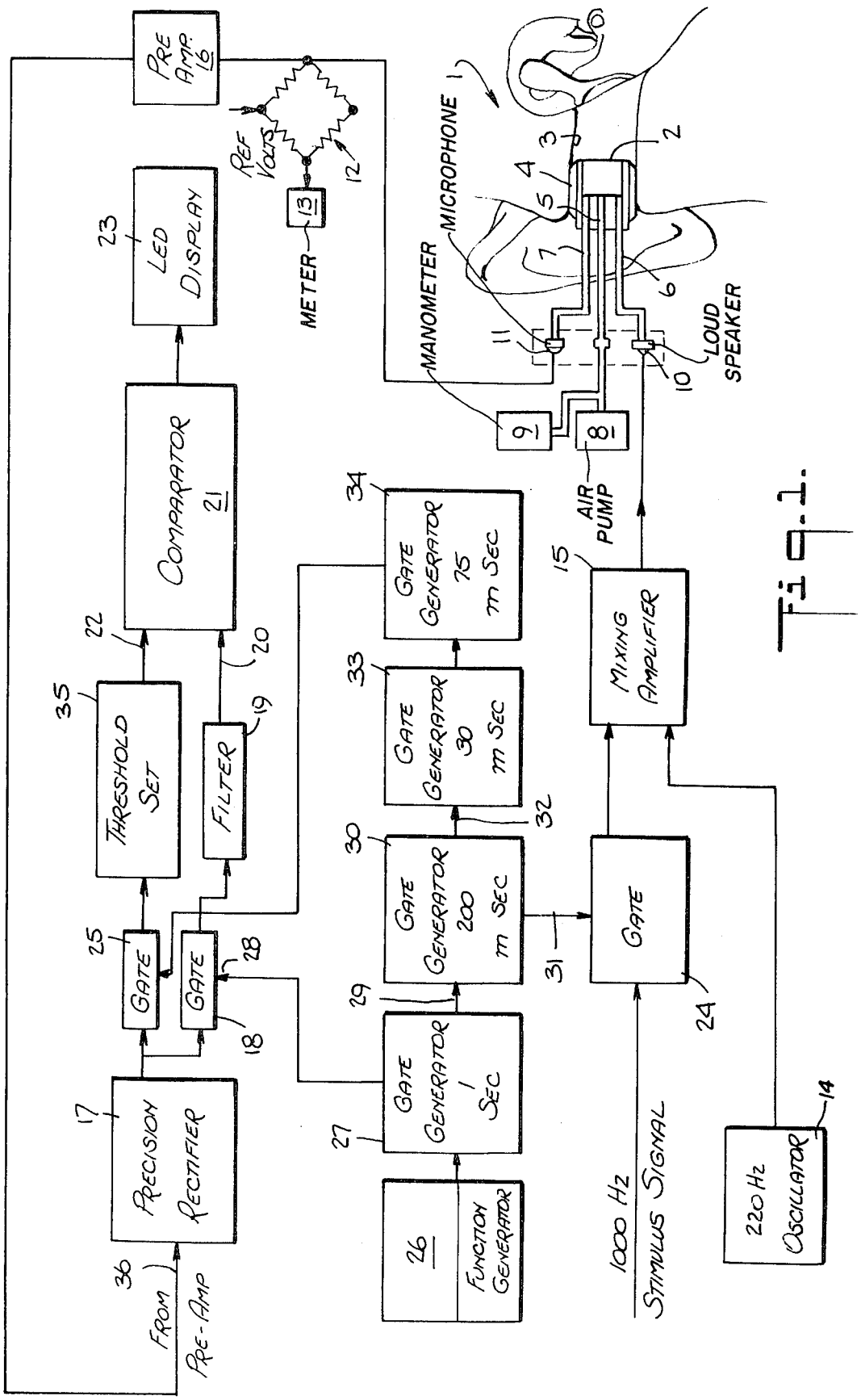
FIG. 1 is a diagrammatic illustration of a preferred embodiment of an improved ipsilateral reflex test system for performing the reflex test method of the invention.

The improved acoustic reflex test described herein is a clinical test which provides information about the function and integrity of the ear. It measures the sound level at which the ear stapedial muscle contracts reflexively. In the presently known testing, one of the patient's ears is sealed off with a probe with the air pressure of the sealed ear canal being set for maximum acoustic compliance. A probe or head phone on the opposite ear subjects the opposite ear to a stimulus tone of increasing intensity, the stapedial muscles contract in both ears simultaneously thereby causing a sharp change in the compliance reading for the first ear.

The improvement in the present method is based upon the fact that the stapedial reflex action has a latency or time delay between the application of stimulus and the muscle contraction. In the improved system, the probe is inserted in one ear and the air pressure is adjusted for a maximum compliance reading. A stimulus signal is added to the probe tone at increasing levels until a level is reached which causes the stapedial muscle contraction. The inherent time delay of the stapedial muscle contraction is utilized by turning off the stimulus and by making a second measurement of the compliance during this period. The two compliance readings are compared to determine whether or not the level of the stimulus most recently applied is sufficient to have caused a muscle contraction as indicated by a significant change in the compliance readings.

This method and the preferred embodiment of a system for performing the method will now be more fully described with reference to FIGS. 1 and 3.

The ear 1 under test is shown at the lower right-hand corner of FIG. 1. A test probe 2 has been inserted into the ear 1 to form an airtight seal enclosing the canal 3 using a resilient cuff 4. The probe 2 includes an air transmission tube 5 and two sound transmission tubes 6 and 7.

The air tube 5 is connected to an air pump 8 and a manometer 9 so that the pressure within the ear canal 3 may be adjusted. The canal air pressure may be adjusted by means of known tests for a maximum compliance, i.e., a minimum level of sound output through tube 7 for a given level of sound input through tube 6. The sound transmission tube 6 is coupled to a loud speaker or other acoustic transducer 10 for the probe tone which is transmitted into the ear canal 3 and which also periodically transmits a stimulus tone for the reflex testing. The second sound tube 7 picks up the tone and stimulus signal responses and transmits them to a microphone 11. The elements 8, 9, 10 and 11 may be separately packaged in a suitable enclosure or they may be incorporated in a single common housing which includes the elements of the reflex system which will now be further described. A bridge 12 and a meter 13 may also be included for determing the maximum compliance or minimum output for a given probe tone level.

The reflex system provides a probe tone, such as a 220 Hertz signal, from a signal source 14. This signal is fed through a mixing amplifier 15 to the speaker 10 and through tube 6 into the ear canal 3. The response from the sealed ear canal is picked up at the microphone 11 and is fed through a preamplifier 16 to a precision rectifier 17. In the normal condition which is the condition in the absence of the stimulus signal, the output of the precision rectifier 17 passes through a normally opened gate 18 into an integrating filter 19 which stores a charge whose voltage level is proportional to the compliance for the sealed ear 3. The filter 19 output is applied to one input terminal 20 of a comparator circuit 21.

The remaining elements of the reflex test system, which will now be described, are provided to apply a stimulus signal to the sealed ear 3 at increasing sound levels for a stimulus period until a level is reached at which the stapedial muscle contracts. They also switch the probe tone compliance signal to a second comparator input 22 for a short period during the stapedial muscle reflex delay time to permit a comparison of the relative compliance levels of the probe tone, i.e., before and after the stimulus signal. The comparator 21 is set to give an output signal when the contraction of the stapedial muscle causes a significant difference thereby generating an output signal in the comparator 21 which activates the light emitting diode display 23.

The portions of the reflex system which provide this operation are the following. The stimulus signal is fed into the mixing amplifier 15 through a gate 24. The signals from the probe 2 are alternately fed to one or the other of comparator inputs 20 and 22 for the above described action through gate 18 and an additional gate 25. A time division or gate control means is shown at the center of FIG. 1 for providing the necessary gate control. This system operates in the following manner.

When it is desired to apply the stimulus signal at a pre-set level, a command signal from a suitable function generator 26 is applied to the first gate generator 27. This signal may be, as illustrated in the top line on FIG. 3, a one second multi-volt step. The application of this signal to the first gate generator 27 feeds a one second off signal at 28 to the normally open gate 18 thereby cutting off the compliance probe tone from the filter 19.

A second output 29 from the first gate generator 27 activates a second gate generator 30 causing its output 31 to open the stimulus gate 24 for a 200 milli-second stimulus period during which time the stimulus is applied through the speaker 10 to the ear canal 3. The second gate generator 30 simultaneously feeds a control signal at 32 to a third gate generator 33 which after a 30 milli-second delay activates the fourth gate generator 34 which opens the gate 25 feeding the compliance tone signal through a threshold set 35 to the second input 22 of comparator 21.

At this point, the first comparator input 20 has applied to it the normal probe tone response generated prior to the contraction of the stapedial muscle. The second input 22 is receiving a probe tone response generated within the delay period during which the stapedial muscle may contract after being subject to the 200 milli-second stimulus signal.

If the stimulus signal, which may be 1000 Hz, has been of sufficiently high level to cause a contraction of the stapedial muscle, this signal at input 22 will be substantially different from the other comparator input 20 resulting in an output signal which will activate the diode display 23 giving the reflex indication. If no diode signal is generated, the operator raises the stimulus level to the next higher step and repeats the operation until a diode signal is received. The level of the stimulus which is recorded when a contraction is indicated provides the necessary clinical data for an evaluation of the condition of the ear under test.

FIG. 2 illustrates in more detail a preferred embodiment of the ipsilateral test system.

At the top of FIG. 2, the terminal 36 for the probe output is shown connected to the precision rectifier 17 through a clamp which functions to prevent an overload of this measurement portion of the circuit. The output of the rectifier 17 is coupled to the two control gates 18 and 25 which comprise 2N5640 F.E.T.'s 40 and 41 and which switch the input between the two terminals 20 and 22 of the comparator 21 during the periods described above whereby a change in the compliance is detected resulting from the significant signal change caused by a contraction of the stapedial muscle at some level of the stimulus signal. The transistor 41 is coupled to the comparator 21 through the adjustable threshold set 35 to permit the comparator input signal differences to be set at a meaningful level. The transistor 40 is coupled to the comparator 21 through the capacitor 42 and resistor 43 of the integrator filter 19. The comparator 21 is a high gain amplifier with the feed-back 44 illustrared and also including an RC feedback coupling 45, 46 for providing a holding action to give an observable indication of sufficient length for the light emitting diode 23.

The four above described gate generators 27, 30, 33 and 34 include field effect transistors 48, 49 and 50 comprising 2N5640's. The transistor 47 may be a 2N2484. The gates are coupled as indicated to provide the above described time delayed switching signals. The additional gate 24 may also include a similar F.E.T. 51 as indicated. It is coupled to the mixing amplifier 15 which completes the circuit with its output 52 coupled to the probe transducer or speaker 10.

It will be seen that an improved method and apparatus have been disclosed for performing a clinical reflex test where the procedure is simplified and the effectiveness of the test is improved by the application of the test probe to the single ear under test.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

Having thus described our invention, we claim:

1. An improved method of reflex testing for a contraction of the stapedial muscle of the ear when subjected to a stimulus signal by measuring a change in the relative acoustic impedance of the middle ear system comprising the steps of:
   obtaining a measure of the relative acoustic impedance of the ear under test using a probe tone;
   subjecting the same ear to a stimulus signal;
   thereafter terminating the stimulus signal;
   obtaining a second measure of the relative acoustic impedance of the ear under test during the reflex response latency period after the termination of the stimulus signal;

comparing the two said acoustic impedance measurements; and generating a signal when the said measures differ.

2. The method as claimed in claim 1 in which said acoustic impedance measure is a compliance.

3. The method as claimed in claim 1 which further comprises the step of sealing the ear canal airtight prior to the impedance tests.

4. The method as claimed in claim 3 which further comprises the step of adjusting the air pressure for the measurements of relative compliance to the pressure of maximum compliance.

5. The method as claimed in claim 1 in which the stimulus signal is increased or decreased in intensity for establishing the reflex measurement.

6. The method as claimed in claim 1 in which the level of the first measure of the acoustic impedance is stored during the periods of the second measurement of acoustic impedance and the reflex response latency period.

7. The method as claimed in claim 1 which further comprises the step of providing a delay period between subjecting the ear to said stimulus signal and the obtaining of the said second measure of the acoustic impedance.

8. The method as claimed in claim 1 which further comprises the step of limiting the generation of said signal until the measures differ by a predetermined amount.

9. An apparatus for reflex testing for a contraction of the stapedial muscle of the ear when subjected to a stimulus signal by measuring a change in the relative acoustic impedance of the middle ear system comprising the combination of:

means for obtaining a measure of the relative acoustic impedance of the ear under test including a probe and a source of probe tone coupled to said probe;

means coupled to the said probe for subjecting the same ear to a stimulus signal for a predetermined period;

means coupled to said probe for obtaining a second measure of the relative acoustic impedance of the ear under test during the reflex response latency period; and comparator means coupled to said first and second measurement means for comparing the two said acoustic impedance measurements.

10. The apparatus as claimed in claim 9 in which said means for obtaining the first and second measurement comprises means for measuring relative compliance.

11. The apparatus as claimed in claim 9 which further comprises means for generating a signal when said first and second measurements differ by more than a predetermined value.

12. The apparatus as claimed in claim 11 in which said signal means comprises a light emitting diode.

13. The apparatus as claimed in claim 9 in which said means for measuring acoustic impedance comprise an ear probe including a seal, an air inlet, a microphone and a sound transducer.

14. The apparatus as claimed in claim 9 in which said means for subjecting the ear to said stimulus signal comprises a timing gate with its input coupled to a stimulus signal, a mixing amplifier, said gate output and said source of probe tone being coupled to mixing amplifier inputs.

15. The apparatus as claimed in claim 14 in which the means for obtaining the second measure of acoustic impedance comprises a comparator circuit, a second gate for uncoupling the impedance signal from a first comparator input, and additional gate means to apply the impedance signal to a second comparator input for a predetermined time period after the stimulus period.

16. The apparatus as claimed in claim 15 which further comprises a delay means for delaying the operation of said additional gate means for a predetermined period.

* * * * *